(12) United States Patent
Clevenger et al.

(10) Patent No.: US 9,872,938 B2
(45) Date of Patent: Jan. 23, 2018

(54) METHODS, COMPOSITIONS AND TECHNIQUES FOR POLYDIMETHYLSILOXANE SURFACE MODIFICATIONS

(71) Applicant: Orthobond, Inc., North Brunswick, NJ (US)

(72) Inventors: Randy Clevenger, North Plainfield, NJ (US); Se-Ho Kim, North Brunswick, NJ (US); Jordan Katz, Short Hills, NJ (US); Carlos Caicedo-Carvajal, North Brunswick, NJ (US)

(73) Assignee: Orthobond, Inc., North Brunswick, NJ (US)

( * ) Notice: Subject to any disclaimer, the term of this patent is extended or adjusted under 35 U.S.C. 154(b) by 0 days.

(21) Appl. No.: 15/162,328

(22) Filed: May 23, 2016

(65) Prior Publication Data

US 2016/0340461 A1 Nov. 24, 2016

Related U.S. Application Data (60) Provisional application No. 62/165,573, filed on May 22, 2015.

(51) Int. Cl.
*C08F 283/12* (2006.01)
*A61L 27/54* (2006.01)
*A61L 27/18* (2006.01)

(52) U.S. Cl.
CPC ............. *A61L 27/54* (2013.01); *A61L 27/18* (2013.01); *A61L 2300/208* (2013.01); *A61L 2300/404* (2013.01); *A61L 2430/04* (2013.01); *C08F 2438/01* (2013.01)

(58) Field of Classification Search
CPC ............................. C08G 77/38; C08F 283/12
See application file for complete search history.

(56) References Cited

U.S. PATENT DOCUMENTS

| | | |
|---|---|---|
| 2002/0161065 A1* | 10/2002 | DiTizio ............... A61L 27/34 522/1 |
| 2011/0182960 A1 | 7/2011 | Wilhelmina et al. |
| 2012/0123012 A1 | 5/2012 | Rheinberger et al. |
| 2013/0040519 A1 | 2/2013 | Locklin et al. |
| 2014/0323676 A1 | 10/2014 | Mehrabi et al. |
| 2014/0357713 A1 | 12/2014 | Damaj et al. |

OTHER PUBLICATIONS

Rubino (J. Infect. Dev. Ctries, 8(9) (2014) 1089-1095).*
Thompson et al. Synthesis and Applications of Heterobifunctional Poly(ethylene oxide) Oligomers. Polymer, vol. 49, 2008, pp. 345-373; Abstract; p. 365, col. 2, Paragraph 4, 29 pages.
Nakayama, et al. Photocurab,e surgical t ssue adhesive glues composed of photoreactive gelatin and po y(ethytene glycol) diacrylate. Journal of biomedical materials Research, vol. 48, 1999, pp. 511-521; abstract, p. 513, col. 1, paragraph 3, 12 pages.
Uzarski, Jr. Reflection Absorption Intrared Spectroscopic Studies of Surface Chemistry Relevant to Chemical and Biolog ca Warfare Agent Defense. Jan. 19, 2009, pp. 1-269 [online], !retrieved on 2016-07-251. Retrieved from the Internet URL: http://theses 1.b.vt.eduithesesiavailableletd-02032009-052713/unrestricted/JUzarski_Dissertation_ETD.pdf: p. 76, paragraph 2, 99 pages.
International Search Report and Written Opinion for PCT Application No. PCT/US2016/033795 dated Aug. 22, 2016, 17 pages.

* cited by examiner

*Primary Examiner* — Kuo-Liang Peng
(74) *Attorney, Agent, or Firm* — Lowenstein Sandler LLP (57) ABSTRACT

Disclosed are novel compositions and methods for making a polymer substrate and a ligand that includes a proximal portion with a photoactive compound bound to the polymer substrate, a terminal portion with an anti-infective/antimicrobial compound, and a reactive portion attaching the proximal portion and the terminal portion.

68 Claims, 3 Drawing Sheets

METHODS, COMPOSITIONS AND TECHNIQUES FOR POLYDIMETHYLSILOXANE SURFACE MODIFICATIONS

FIELD OF INVENTION

The present disclosure is directed to methods, compositions and techniques for modifying the surface of polymers, such as polysiloxanes (e.g., polydimethylsiloxanes or PDMS also referred to as silicones). The modified surface of the polymers may then be used to attach anti-microbial (e.g., anti-infective) compounds, such as quaternary ammonium or phosphonium compounds, to create an antimicrobial surface. These modified surfaces may then be used to create medical devices and implants, such as breast implants.

BACKGROUND

Microbial infections pose a serious health risk, particularly for those undergoing medical procedures, such as surgery. Typically, infection prevention may be achieved by the topical application of disinfectants, antiseptics and antibacterials to surfaces likely to be contacted by infectious agents. However, many of these compounds are harmful to mammalian tissue, only have a short-term effect and need to be reapplied constantly for infection prevention. Those patients that do contract a microbial infection may be able to treat the infection with an antibiotic. However, the antibiotic may not be effective and, even if the patient may be treated with an antibiotic, the infection alone can still cause serious harm to the patient.

A patient may be particularly susceptible to infection during surgery or when a medical device is implanted in the patient since there is two-fold exposure from the surgery itself as well as the medical device. There remains a need decrease the instances of infection by treating the surface material of the medical devices to help prevent infections.

Silicones are an increasingly important polymer for both medical and non-medical applications. For medical devices in particular, silicones may be used for seals, gaskets, valves, masks, catheters, tubing, breast implants among other devices. With the growing popularity for silicones in use with medical devices, there is also a growing need to make silicones more resistant as a source for infection.

There exists a need in the art for a compositions, methods and techniques to create surface modifications to polysiloxanes (e.g., polydimethyl siloxanes such as silicones) and to attach anti-microbial (e.g., anti-infective) agents to the surface of polysiloxanes (e.g., silicones).

OBJECTS AND SUMMARY OF THE INVENTION

It is an object of certain embodiments of the present invention to provide for a composition with a polymer substrate and a ligand bound to the polymer, where the ligand has a photoactive portion bound to the polymer substrate, an anti-microbial (e.g., an anti-infective) portion and a reactive portion connecting the photoactive and the anti-microbial portions.

It is an object of certain embodiments of the present invention to provide for a composition containing a polysiloxane (e.g., a silicone) which has been modified with an anti-microbial (e.g., an anti-infective compound), such as a quaternary ammonium compound or phosphonium compound.

It is an object of certain embodiments of the present invention to provide for a composition containing a bifunctional linker molecule that is able to covalently bond to the surface of a polymer substrate, such as a polysiloxane (e.g., a silicone), and allows for additional modification, such as the attachment of an anti-microbial (e.g., an anti-infective) compound.

It is an object of certain embodiments of the present invention to provide for a composition including a polysiloxane (e.g., a silicone) and an attached ligand where the ligand is modified to have a portion that can covalently bond to the polysiloxane surface and another portion that includes an anti-microbial (e.g., an anti-infective agent), such as a quaternary ammonium or phosphonium compound.

It is an object of certain embodiments of the present invention to provide for a composition for medical devices where the medical device includes a surface-modified polysiloxane (e.g., silicone) with covalently-bonded, anti-microbial (e.g., anti-infective agents).

It is an object of certain embodiments of the present invention to provide for a method of modifying the surface of a polysiloxane (e.g., a silicone) with bound anti-microbial (e.g., anti-infective) agents.

It is an object of certain embodiments of the present invention to provide for a method of making a bifunctional linker molecule that is able to covalently bond to the surface of a polysiloxane (e.g., a silicone) polymer substrate and allows for additional modification, such as attaching an anti-microbial (e.g., an anti-infective) compound.

DETAILED DESCRIPTION

By virtue of the present invention, in one embodiment, there is provided a composition comprising a polymer substrate, where the polymer substrate may be a polysiloxane (e.g., a silicone), and a ligand which may be bound to the polymer substrate, the ligand comprising (i) a proximal portion based on a photoactive compound, the proximal portion bound to the polymer substrate, (ii) a terminal portion comprising an anti-microbial (e.g., an anti-infective) compound, and (iii) a reactive portion attaching the proximal portion and the terminal portion. In some embodiments, the polymer substrate may be covalently bound to the ligand.

In other embodiments, the polymer substrate may be, but is not limited to polyamides, polyurethanes, polyureas, polyesters, polyketones, polyimides, polysulfides, polysulfoxides, polysulfones, polythiophenes, polypyridines, polypyrroles, polyethers, polyetheretherketones, polyetherketoneketones, polysiloxanes (e.g., polydimethyl siloxanes such as silicones), polysaccharides, fluoropolymers, amides, imides, polypeptides, polyethylene, polystyrene, polypropylene, glass reinforced epoxies, liquid crystal polymers, thermoplastics, bismaleimide-triazine (BT) resins, benzocyclobutene polymers, Ajinomoto Buildup Films (ABF), polyethylene terephthalate (PET), polyetheretherketones (PEEK), polyetherketoneketones (PEKK), nylon, low coefficient of thermal expansion (CTE) films of glass and epoxies, and composites. Such functionalized polymer surfaces can be used to covalently bond a ligand with antimicrobial (e.g., an anti-infective) agent on the surface. In some embodiments, the polymer substrate may be a polysiloxane (e.g., a silicone).

In some embodiments of the composition, the proximal portion (e.g., the linker) may consist of the following formula:

where A and B can each be independently selected from a 5-membered aromatic, a 5-membered heteroaromatic, a 6-membered aromatic, and a 6-membered heteroaromatic; Y can be a moiety selected from hydrogen, hydroxyl, halogen and optionally substituted alkyl; X can be a moiety selected from O, S, SO—, —SO$_2$—, —(CR$^{1a}$R$^{1b}$)—, —NR$^2$—, —SO$_2$NR$^2$—, and —NR$^2$SO$_2$—, where R$^{1a}$ and R$^{1b}$ can be independently selected from a group consisting of hydrogen, halogen, and alkyl and R$^2$ can be selected from hydrogen and alkyl; R$^3$ can include the polymer substrate; and can include R$^4$ the reactive portion.

In other embodiments, the polymer substrate may be bound to the carbon linking A and B. In still other embodiments, at least one of A or B may be a phenyl moiety or both A and B may be a phenyl moiety. In some embodiments, Y may be a hydroxyl group and/or X may be O.

In some embodiments, the ligand may be bond to the polymer substrate through photoactive or non-photoactive compounds. In some embodiments, if the ligand includes a photoactive compound, the photoactive compound may be activated by UV light or UV radiation.

In other embodiments, the reactive portion may comprise of an optionally substituted alkane. For example, the alkane can be substituted with O. In some other embodiments, the alkane may consist of from about 1 to about 100 carbons or from about 5 to about 15 carbons.

In some embodiments, the reactive portion may consist of a polyethylene glycol. In other embodiments, the terminal portion may comprise a methacrylate moiety. In still other embodiments, the terminal portion may be derived from 12-methacryloyloxydodecylpyridinium bromide.

In some embodiments, the anti-microbial (e.g., anti-infective) compound may be antimicrobials, antibiotics, antifungals, antiseptics, disinfectants, and preservatives. In other embodiments, the anti-microbial compound may include, but is not limited to, amikacin, gentamicin, kanamycin, neomycm, netilmicin, tobramycin, paromomycin, geldanamycin, herbimycin, loracarbef, ertapenem, doripenem, imipenem/cilastatin, meropenem, cefadroxil, cefazolin, cefalotin, cefalexin, cefaclor, cefamandole, cefoxitin, cefprozil, cefuroxime, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycm, telavancin, clindamycin, lincomycin, daptomycin, azithromycin, clarithromycin, dirithromycin, erythromycin, roxithromycin, troleandomycin, telithromycin, spectinomycin, spiramycin, aztreonam, furazolidone, nitrofurantoin, amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, penicillin g, temocillin, ticarcillin, amoxicillin/clavulanate, ampicillin/sulbactam, piperacillin/tazobactam, ticarcillin/clavulanate, bacitracin, colistin, polymyxin b, ciprofloxacin, enoxacin, gatifloxacin, levofloxacin, lomefloxacin, moxifloxacin, nalidixic acid, norfloxacin, ofloxacin, Irovafloxacin, grepafloxacin, sparfloxacin, temafloxacin, mafenide sulfonamidochrysoidine, sulfacetamide, sulfadiazine, silver sulfadiazine, sulfamethizole, sulfamethoxazole, sulfanamide, sulfasalazine, sulfisoxazole, trimethoprim, trimethoprimsulfamethoxazole, demeclocycline, doxycycline, minocycline, oxytetracycline, tetracycline, clofazimine, dapsone, capreomycm, cycloserine, ethambutol, ethionamide, isoniazid, pyrazinamide, rifampicin, rifabutin, rifapentine, streptomycin, arsphenamine, chloramphenicol, fosfomycin, fusidic acid, linezolid, metronidazole, muplrocm, platensimycin, quinupristin/dalfopristin, rifaximin, thiamphenicol, tigecycline, tinidazole, chlorhexidine, biguanides, colloidal silver, silver nitrate, mercury chloride, phenylmercury salts, copper, copper sulfate, copper oxidechloride, phosphoric acid, nitric acid, sulfuric acid, amidosulfuric acid, toluenesulfonic acid, sodium hydroxide, potassium hydroxide, calcium hydroxide, quaternary ammonium compounds, quaternary ammonium dendrimers, phosphonium compounds, pharmaceutically acceptable salts thereof or combinations thereof. In other embodiments, the anti-microbial (e.g., anti-infective) compound may be selected from a quaternary ammonium compound or a phosphonium compound.

According to certain embodiments of the disclosure, the ligand attached to the surface of the polymer substrate can be selected from the following:

(I)

(II)

(III)

(IV)

and (V)

wherein, x, y and n are independently integers from 0 to 100.

Figure 1:
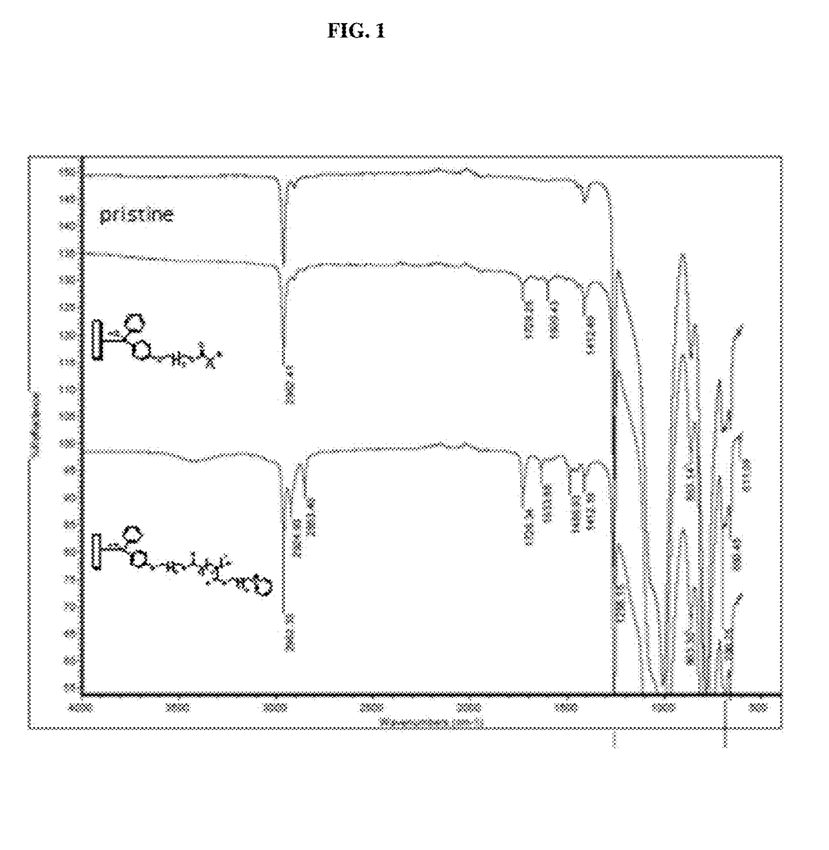
FIG. 1 shows infrared spectroscopies of treated surfaces showing successful attachment of the displayed functional groups to a silicone surface.
Figure 2:
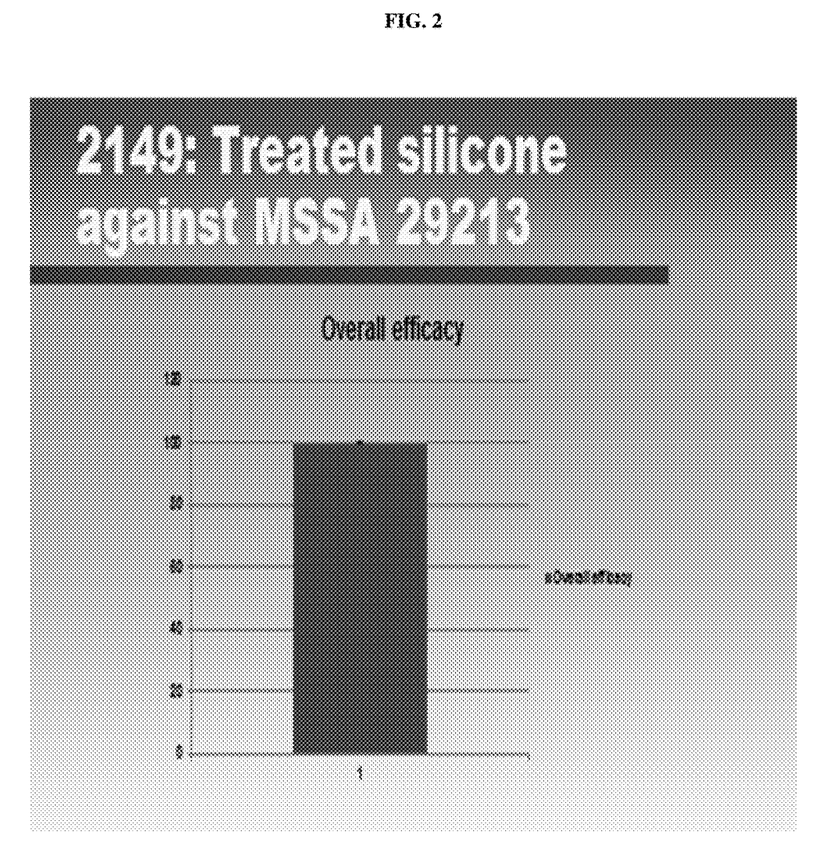
FIG. 2 shows results of an assay (e.g., ASTM E2149) performed to measure the antimicrobial efficacy of the treated surfaces. The results indicate that, against *S. aureus* (MSSA 29213), the surfaces achieved about 99.99% (or 4 logs) of killing.
Figure 3:
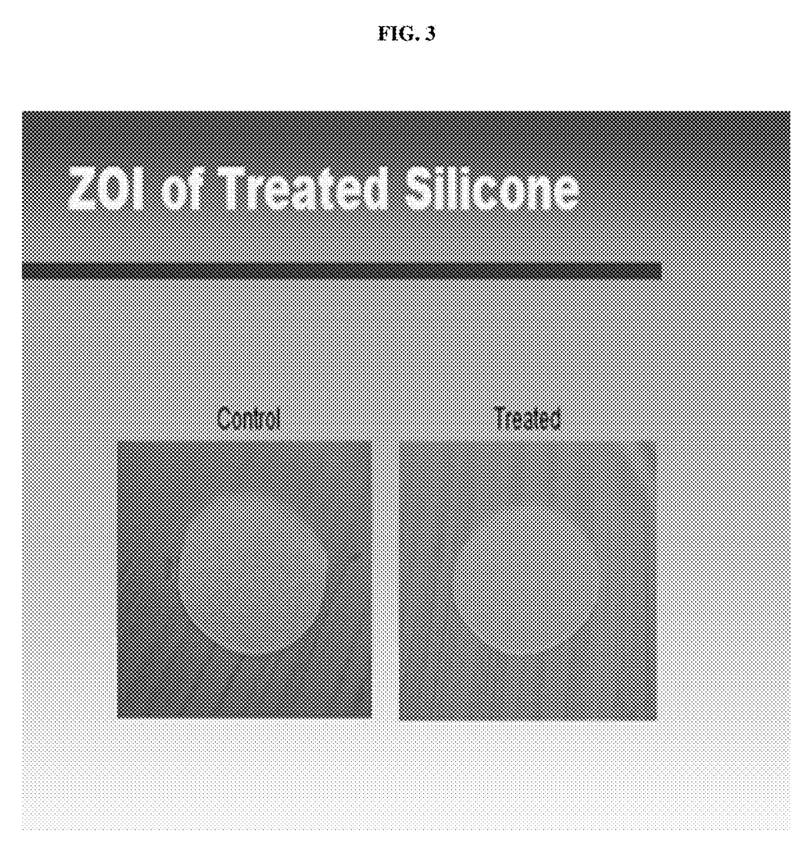
FIG. 3 shows the results of a zone of inhibition (ZOI) assay indicating treated surfaces were non-eluting (e.g., covalently bound) by virtue of showing no zone of inhibition.

FIG. 1 the shows infrared spectroscopies of treated surfaces showing successful attachment of the displayed antimicrobial (e.g., anti-infective) functional groups to the silicone surface. FIG. 2 shows the overall efficacy of the treated surfaces in killing *S. aureus* (MSSA 29213). An ASTM E2149 assay was used to demonstrate the modifications to the treated surfaces resulted in about 99.99% (or 4 logs) efficacy in killing the *S. aureus*. FIG. 3 shows the results of a zone of inhibition ("ZOI") assay. The ZOI assay shows the anti-microbial (e.g., anti-infective) agent is non-eluting and therefore covalently bonded to the silicone surface since there is no apparent zone of inhibition.

In some embodiments, the polymer substrate may be a medical device. In other embodiments, the substrate may be a medical device that is implantable. In some embodiments, the types of medical devices that may be used with this invention include, but are not limited to endoscopic, arthroscopic, laproscopic, cardiac, cardiovascular, vascular, orthopedic, orthopedic trauma or spinal. Medical devices that may be used in this invention may include, but are not limited to medical devices including implants, screws, rods, pins, catheters, stents, shunts, tapes, meshes, ropes, cables, wires, sutures, staples, surgical tools and the like. In some particular embodiments, the polymer substrate may be a breast implant.

In some embodiments, the composition comprises a polymer substrate and a ligand covalently bound to the polymer substrate, the ligand comprising (i) a proximal portion, the proximal portion bound to the polymer substrate, (ii) a terminal portion comprising an anti-microbial compound, and (iii) a reactive portion attaching the proximal portion and the terminal portion.

According to certain embodiments of the disclosure, the area density of the anti-microbial compound on the surface of the polymer substrate can be from about $1 \times 10^{14}$ molecules/cm$^2$ to about $1 \times 10^{19}$ molecules/cm$^2$, or from about $1 \times 10^{15}$ molecules/cm$^2$ to about $1 \times 10^{18}$ molecules/cm$^2$. Loading of the anti-microbial compound on the surface of the polymer substrate can be from about 10 ng/cm$^2$ to about 1000 ng/cm$^2$, or from about 100 ng/cm$^2$ to about 500 ng/cm$^2$, or from about 200 ng/cm$^2$ to about 300 ng/cm$^2$. The thickness of the ligand on the surface of the polymer substrate can be from about 10 nm to about 1 μm, or about 100 nm to about 500 nm, or about 1 μm or less. Materials having modified surfaces according to the various embodiments of the disclosure will retain their surface modified characteristics when stored dry, in a storage container at a temperature of about 40° F. to about 110° F. for about 1 month or longer, or about 6 months or longer, or about 1 year or longer, or about 2 years or longer or about 4 years or longer.

The present disclosure further relates to methods for modifying the surfaces of substrates, for example, polymers, such as polysiloxanes (e.g., silicones). Certain embodiments relate to a method of modifying a surface of a polymer substrate including (a) applying a composition to a surface of the polymer substrate, the composition comprising a linker attached to a reactive portion; (b) applying photocatalytic ultraviolet light to the surface to attach the linker to the polymer substrate; and (c) attaching a terminal portion comprising an anti-microbial compound to the reactive portion using atom transfer radical polymerization to render the surface antimicrobial. The linker can be a compound as described above and in certain aspects, the anti-microbial compound can be a quaternary ammonium compound or a phosphonium compound. The polymer substrate can include a polysiloxane material such as a polydimethylsiloxane. The polymer substrate can be an implantable a medical device such as a breast implant. In certain embodiments, the polymer substrate can be covalently bound to the ligand.

In certain embodiments, the composition applied to the surface is [4-[(11-undecyloxy-α-bromoisobutryl)-oxy]phenyl]phenyl methanone (2a) ("benzophonone initiator"). The composition can be applied via spraying onto the surface or via an applicator such as a brush (i.e., brushing the composition onto the surface).

In certain embodiments, the photocatalytic ultraviolet light can be applied at a wavelength of about 500 nm or less, or about 400 nm or less, or about 370 nm or less, or about 300 nm or less, or about 254 nm or less. The ultraviolet light can be applied at an intensity of about 5 mW/cm$^2$ or less, or about 10 mW/cm$^2$ or less, or about 50 mW/cm$^2$ or less, or about 100 mW/cm$^2$ or less, or about 1000 mW/cm$^2$ or less. The surface of the substrate having the composition thereon can be irradiated with the ultraviolet light for about 1 h or less, or about 2 h or less, or about 5 h or less, or about 10 h or less, or about 20 h or less, or about 30 h or less.

In certain embodiments of the disclosure, a modified benzophenone compound can be used to attach a linker to a substrate surface (e.g., the surface of a silicone substrate) using photocatalytic ultraviolet light. The resulting modified surface can be further modified using an Atom Transfer Radical Polymerization ("ATRP") reaction to render the surfaces antimicrobial.

In one embodiment, the linker can be prepared beginning with a mixture of an organic polymerization initiator (e.g., 4-hydroxybezophenone) and an organic alcohol (e.g., 11-bromoundecanol) dissolved in a solvent (e.g., dimethylformamide or "DMF"), which can then be added to a basic compound (e.g., K$_2$CO$_3$). The combination can be stirred for about 12 hours to about 36 hours, or for about 18 hours to about 30 hours, or for about 22 hours to about 26 hours, or for about 24 hours or longer. The stirred combination can be further mixed with about 100 mL to about 500 mL of water and stirred for about 15 minutes to about 45 minutes, or for about 30 minutes or longer, resulting in the formation of a solid precipitate. The solid precipitate can be filtered, washed with one or more solvents (e.g., water, ether, and hexane), and dried (e.g., over air) to produce the an intermediate compound (e.g., methanone, [4-[(11-hydroxyundecyl)oxy]phenyl]phenyl-methanone).

A solution containing the intermediate compound dissolved in a solvent (e.g., CH$_2$CH or CH$_2$Cl$_2$ at about 50 mL to about 150 mL) can be treated with an amine compound (e.g., triethylamine or "NEt$_3$"), followed by addition of an acid halide (e.g., α-isobutyryl bromide at about 0.5 mL to about 5.0 mL, or about 1.0 mL to about 2.0 mL about (e.g., 10 mmol to about 20 mmol, or about 12 mmol to about 16 mmol) at a temperature of about −10° C. to about 10° C., or about 0° C. The resulting mixture can be warmed to room temperature and stirred for about 4 hours. Upon completion, the mixture can be diluted with a solvent (e.g., CH$_2$CH, CH$_2$Cl$_2$), washed with a brine, and dried (e.g., using Na$_2$SO$_4$), filtered, and concentrated in vacuo. The crude can be purified by any suitable method known to those of ordinary skill in the art, for example, by column chromatography (SiO$_2$, gradient from about 2% to about 10%, ethyl acetate or "EtOAc" in hexane) to produce a linker according to various example aspects of the disclosure.

Preparing a modified surface composition according to example aspects of the disclosure, can include applying a composition to a surface of a polymer substrate (e.g., a polysiloxane material such as a silicone material or implant), the composition having a linker attached to a reactive portion; applying photocatalytic ultraviolet light to the surface to attach the linker to the polymer substrate; and attaching a terminal portion comprising an anti-microbial (e.g., anti-infective) compound to the reactive portion using atom transfer radical polymerization to render the surface antimicrobial. The composition including the linker can be prepared as described above, and in certain aspects can include a silane terminated linker.

In one embodiment, a solution of linker in acetone (e.g., about 5 mg to about 15 mg in about 0.1 mL to about 10 ml, or about 0.5 ml or more of acetone per disc) can be deposited on a substrate surface (e.g., a polysiloxane (e.g., a silicone) disc (#30)) and smeared evenly on the surface. The substrate can then be irradiated with photocatalytic ultraviolet light (e.g., about 500 nm or less, or about 370 nm or less, or about 255 nm to about 365 nm) for about 10 minutes to about 50 minutes, or for about 30 minutes or longer. The substrates can be rinsed with one or more solvent (e.g., ethanol and acetone), sonicated in a solvent (e.g., acetone) for about 1 minute to about 5 minutes, or for about 2 minutes or longer, purged with $N_2$ and dried in vacuo to produce the modified surface.

In another embodiment, a reaction chamber can be charged with an antibacterial solution of an antibacterial compound (e.g., methacryloyloxydodecylpyridinium bromide or "MDPB") and water. A substrate (e.g., a polysiloxane such as a silicone substrate) can then be placed in the reaction chamber. Separately, a tridentate ligand (e.g., pentamethyldiethylenetriamine or "PMDETA") can be added to a stirred suspension of CuBr and $H_2O$. After stirring for about 15 minutes to about 45 minutes, or for about 30 minutes or longer, the copper-complex solution can be added the antibacterial solution and the resulting mixture stirred for about 4 hours to about 24 hours. The substrate can be removed from the reaction chamber, rinsed with water, a solvent (e.g., ethanol), sonicated in a solvent (e.g., ethanol) for about 2 minutes to about 10 minutes, or for about 2 minutes or longer, purged with $N_2$, and dried in vacuo to produce a modified surface.

Whereas many alterations and modifications of the disclosure will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims, which in themselves recite only those features regarded as the disclosure.

EXAMPLES

Example 1

A modified benzophenone is used to attach the linker to the surface of a silicone via the application of photocatalytic ultraviolet light. The resulting surface-modified silicone was further modified using an Atom Transfer Radical Polymerization (ATRP) to render the surfaces antimicrobial.

Preparation of the Linker 2a

A mixture of 4-hydroxybezophenone (6.00 g, 30.3 mmol) and 11-bromo-1-undecanol (8.40 g, 33.3 mmol) in dimethylformamide (DMF) (30 mL) was added $K_2CO_3$ (6.28 g, 45.4 mmol). After stirring for 1 day, the mixture was poured with water (300 mL) and stirred for 30 minutes. The solid precipitate was filtered, washed with water, ether (10 mL), and hexane, and dried over air to produce methanone, [4[(11-hydroxyundecyl)oxy]phenyl]phenyl-methanone (11 g, 99%).

A solution of methanone, [4[(11-hydroxyundecyl)oxy] phenyl]phenyl-methanone (5.00 g, 13.6 mmol) in $CH_2Cl_2$ (100 mL) was treated with N,N-diethylethanamine ("$NEt_3$") (4.52 mL, 3.39 mmol), followed by addition of α-isobutyryl bromide (1.84 mL, 14.9 mmol) at 0° C. The resulting mixture was slowly warmed up to room temperature and stirred for 4 hours. Upon completion, the mixture was diluted with $CH_2Cl_2$, washed with brine, dried ($Na_2SO_4$), filtered, and concentrated in vacuo. The crude was purified by column chromatography ($SiO_2$, gradient from 2% to 10%, ethyl acetate or "EtOAc" in hexane) to produce Compound 2a (shown in the formula below) as pale yellow oil (6.2 g, 88%).

The chemical formula for the reaction in Example 1 is presented below:

where (a) is 11-bromo-1-undecanol, $K_2CO_3$, DMF, rt, and (b) is α-bromoisobutyryl bromide, $CH_2Cl_2$, rt.

Example 2

Synthesis of Surface 2a

Silicone discs (#24, 4 $cm^2$ per disc) were rinsed with $H_2O$ (180 mL×3), sonicated in EtOH (180 mL×1) and acetone (180 mL×1) for 10 min, dried in a stream of $N_2$, and further dried under vacuum for 10 min.

The silicone discs (#24) were placed in a glass plate and a solution of benzophenone initiator ("Compound 2a") (16 mg of 2a in 0.3 mL of acetone for each disc) was evenly distributed on the silicon surface. After a brief drying, the surfaces were irradiated with UV (254 nm) with intensity 3-8 mW/$cm^2$ for 3-7 h. The discs were then rinsed with EtOH (150 mL×3), acetone (150 mL×3), sonicated in acetone (180 mL×2) for 10 min, dried in a stream of $N_2$ and further dried in vacuum for 10 min to produce Surface 2a.

Synthesis of Surface 3a

A 500-mL Schlenk tube was charged with MDPB (10.48 g, 2.40 mmol), Surface 2a (#24), and $H_2O$ (280 mL). The flask was evacuated and filled with Ar (×3). In a separate 100-mL Schlenk tube, $H_2O$ (70 mL) was charged. After a three-cycle of evacuation/refilling with Ar, CuBr (875 mg, 6.10 mmol) was added, followed by PMDETA (1.75 mL, 8.38 mmol). The CuBr/PMDETA solution was stirred for 0.5 h and transferred into the above MDPB solution. The resulting mixture was stirred for 15 h. Upon completion, the discs were removed, rinsed with $H_2O$ (250 mL×5) and EtOH (150 mL×3), sonicated in EtOH (200 mL×2) for 10 min, dried in a stream of $N_2$ and further dried in vacuum for 10 min to provide Surface 3a.

The chemical formulas for the reactions in Example 2 are provided below:

surface 1 → surface 2a → surface 3a where (a) is 2a, UV (254 or 365 nm), 3-7 h, 3-8 mW/cm$^2$ and (b) CuBr, PMDETA, H$_2$O, 10-18 h.

Example 3

Synthesis of Compound 2b

Compound 2b was synthesized using a similar process to the synthesis of Compound 2a (described above), using readily available tetraethylene glycol p-toluenesulfonate (55% in two steps) instead of 11-bromo-1-undecanol.

The chemical formula for the reaction in Example 3 is provided below:

where (a) is tetraethylene glycol p-toluenesulfonate, K$_2$CO$_3$, DMF, rt and (b) is α-bromoisobutyryl bromide, CH$_2$Cl$_2$, rt.

Example 4

Synthesis of Surface 2b

Surface 2b was prepared in a similar manner to Surface 2a except Compound 2b (shown above) was used instead of Compound 2a.

Synthesis of Surface 3b

Surface 3b was prepared in a similar manner to Surface 3a except that Surface 2b was used instead of Surface 2a.

The chemical formula for the reactions in Example 4 are provided below:

surface 3b where (a) 2b, is UV (254 or 365 nm), 3-7 h, 3-8 mW/cm² and (b) is CuBr, PMDETA, H₂O, 10-18 h.

Example 5

Synthesis of Surfaces 4a to 4d

Silicon surfaces were functionalized with copolymers of methacryloyloxydodecylpyridinium bromide (MDPB) and poly(ethylene glycol) methacrylate (PEGMA). The random copolymer surfaces 4a-d were synthesized from surface 2a using ATRP of two monomers having various molar ratios.

The chemical formulas for the reactions in Example 5 are provided below:

4a-d where (a) is methacryloyloxydodecylpyridinium bromide (MDPB), poly(ethylene glycol) methacrylate (PEGMA), CuBr, PMDETA, H₂O, 10-18 h. The following Table summarizes the molar ratios of MDPB and PEGMA that were used:

| Surface | Molar ratio | |
|---|---|---|
| | MDPB | PEGMA ($M_n$ 360) |
| 4a | 1 | 0.3 |
| 4b | 1 | 0.6 |
| 4c | 1 | 1 |
| 4d | 1 | 3 |

Synthesis of Surface 4c

A 200-mL Schlenk tube was charged with MDPB (6.00 g, 14.6 mmol), PEGMA (5.19 mL, 14.6 mmol), surface 2a (#16), and H₂O (160 mL). The flask was evacuated and filled with Ar (×3). In a separate 100-mL Schlenk tube, H₂O (40 mL) was charged. After a three-cycle of evacuation/refiling with Ar, CuBr (500 mg, 3.49 mmol) was added, followed by PMDETA (1.00 mL, 4.79 mmol). The CuBr/PMDETA solution was stirred for 0.5 h and transferred into the above MDPB solution. The resulting mixture was stirred for 15 h. Upon completion, discs were removed, rinsed with H₂O (250 mL×5) and EtOH (150 mL×3), sonicated in EtOH (200 mL×2) for 10 min, dried in a stream of N₂ and further dried in vacuum for 10 min to provide surface 4c.

Synthesis of Surfaces 4a, 4b, and 4d

Surfaces 4a, 4b, and 4d were prepared in a similar manner to surface 4c, except that different MDPB and PEGMA molar ratios were used (MDPB:PEGMA molar ratios of 1:0.3, 1:0.6 and 1:3 for 4a, 4b, and 4d, respectively).

What is claimed is:

1. A composition comprising a polymer substrate, wherein the polymer substrate comprises a polysiloxane material, and a ligand covalently bonded to the polymer substrate, the ligand comprising
    (i) a proximal portion based on a photoactive compound, the proximal portion covalently bonded to the polymer substrate,
    (ii) a terminal portion comprising a covalently bonded anti-microbial compound, and
    (iii) a reactive portion covalently attaching the proximal portion and the terminal portion.
2. The composition of claim 1, wherein the polysiloxane material is a polydimethyl siloxane.
3. The composition of claim 1, wherein the proximal portion consists of the following formula:

wherein A and B are each independently selected from a group consisting of a 5-membered aromatic, a 5-membered heteroaromatic, a 6-membered aromatic, and a 6-membered heteroaromatic;

Y is a moiety selected from a group consisting of hydrogen, hydroxyl, halogen, and optionally substituted alkyl; and X is a moiety selected from a group consisting of O, S, SO—, —SO$_2$—, —(CR$^{1a}$R$^{1b}$)—, —NR$^2$—, —SO$_2$NR$^2$—, and —NR$^2$SO$_2$—, wherein R$^{1a}$ and R$^{1b}$ are independently selected from a group consisting of hydrogen, halogen, and alkyl and R$^2$ is selected from a group consisting of hydrogen and alkyl.

4. The composition of claim 3, wherein at least one of A or B is a phenyl moiety.

5. The composition of claim 3, wherein both A and B are a phenyl moiety.

6. The composition of any of claims 3 to 5, wherein Y is a hydroxyl group.

7. The composition of any of claims 3 to 5, wherein X is O.

8. The composition of any of claims 1 to 3, wherein the reactive portion comprises an optionally substituted alkane.

9. The composition of claim 8, wherein the alkane consists of from about 1 to about 100 carbons.

10. The composition of claim 8, wherein the alkane is substituted.

11. The composition of claim 10, wherein the alkane is substituted with O.

12. The composition of claim 9, wherein the alkane consists of from about 5 to about 15 carbons.

13. The composition of any of claims 1 to 3, wherein the reactive portion comprises a polyethylene glycol.

14. The composition of any of claims 1 to 3, wherein the terminal portion comprises a methacrylate moiety.

15. The composition of any of claims 1 to 3, wherein the terminal portion is derived from 12-methacryloyloxydodecylpyridinium bromide.

16. The composition of any of claims 1 to 3, wherein the ligand is selected from a group consisting of:

(I)

(II)

(III)

-continued (IV)

(V)

wherein, x, y and n are independently integers from 0 to 100.

17. The composition of claim 1, wherein the polymer substrate is a medical device.

18. The composition of claim 17, wherein the medical device is implantable.

19. The composition of claim 1, wherein the polymer substrate is a breast implant.

20. The composition of claim 1, wherein the polymer substrate is polydimethylsiloxane.

21. The composition of claim 1, wherein the anti-microbial compound is a quaternary ammonium compound or a phosphonium compound.

22. The composition of claim 1, wherein the photoactive compound is activated by UV light.

23. A method of covalently bonding a ligand to a surface of a polymer substrate, the ligand comprising
(i) a proximal portion based on a photoactive compound, the proximal portion covalently bonded to the polymer substrate,
(ii) a terminal portion comprising a covalently bonded anti-microbial compound, and
(iii) a reactive portion covalently attaching the proximal portion and the terminal portion;
the method comprising:
applying a composition to a surface of the polymer substrate, the composition comprising a linker attached to a reactive portion;
applying photocatalytic ultraviolet light to the surface to attach the linker to the polymer substrate; and
attaching a terminal portion comprising an anti-microbial compound to the reactive portion using atom transfer radical polymerization to render the surface antimicrobial.

24. The method of claim 23, wherein the polymer substrate comprises a polysiloxane material.

25. The method of claim 23 wherein the composition is [4-[(11-undecyloxy-α-bromoisobutryl)-oxy]phenyl]phenyl methanone.

26. The method of any of claims 23 to 25 comprising, applying the composition via spraying onto the surface.

27. The method of any of claims 23 to 25 comprising, applying the composition via an applicator.

28. The method of claim 27, wherein the applicator is a brush.

29. The method of claim 23, wherein the wavelength of the ultraviolet light is about 500 nm or less.

30. The method of claim 23, wherein the wavelength of the ultraviolet light is about 400 nm or less.

31. The method of claim 23, wherein the wavelength of the ultraviolet light is about 370 nm or less.

32. The method of claim 23, wherein the wavelength of the ultraviolet light is about 300 nm or less.

33. The method of claim 23, wherein the wavelength of the ultraviolet light is about 254 nm or less.

34. The method of claim 23, wherein intensity of the ultraviolet light is about 5 mW/cm$^2$ or less.

35. The method of claim 23, wherein intensity of the ultraviolet light is about 10 mW/cm$^2$ or less.

36. The method of claim 23, wherein intensity of the ultraviolet light is about 50 mW/cm² or less.

37. The method of claim 23, wherein intensity of the ultraviolet light is about 100 mW/cm² or less.

38. The method of claim 23, wherein intensity of the ultraviolet light is about 1000 mW/cm² or less.

39. The method of claim 23, wherein applying photocatalytic ultraviolet light to the surface comprises irradiating the surface for about 1 h or less.

40. The method of claim 23, wherein applying photocatalytic ultraviolet light to the surface comprises irradiating the surface for about 2 h or less.

41. The method of claim 23, wherein applying photocatalytic ultraviolet light to the surface comprises irradiating the surface for about 5 h or less.

42. The method of claim 23, wherein applying photocatalytic ultraviolet light to the surface comprises irradiating the surface for about 10 h or less.

43. The method of claim 23 wherein applying photocatalytic ultraviolet light to the surface comprises irradiating the surface for about 20 h or less.

44. The method of claim 23, wherein applying photocatalytic ultraviolet light to the surface comprises irradiating the surface for about 30 h or less.

45. The method of claim 23, wherein the polysiloxane material is a polydimethyl siloxane.

46. The method of claim 23, wherein the linker consists of the following formula:

wherein A and B are each independently selected from a group consisting of a 5-membered aromatic, a 5-membered heteroaromatic, a 6-membered aromatic, and a 6-membered heteroaromatic;

Y is a moiety selected from a group consisting of hydrogen, hydroxyl, halogen, and optionally substituted alkyl; and X is a moiety selected from a group consisting of O, S, SO—, —SO$_2$—, —(CR$^{1a}$R$^{1b}$)—, —NR$^2$—, —SO$_2$NR$^2$—, and —NR$^2$SO$_2$—, wherein R$^{1a}$ and R$^{1b}$ are independently selected from a group consisting of hydrogen, halogen, and alkyl, and R$^2$ is selected from a group consisting of hydrogen and alkyl.

47. The method of claim 46, wherein at least one of A or B is a phenyl moiety.

48. The method of claim 46, wherein both A and B are a phenyl moiety.

49. The method of any of claims 46 to 48, wherein Y is a hydroxyl group.

50. The method of any of claims 46 to 48, wherein X is O.

51. The method of any of claims 46 to 48, wherein the reactive portion comprises an optionally substituted alkane.

52. The method of claim 51, wherein the alkane consists of from about 1 to about 100 carbons.

53. The method of claim 51, wherein the alkane is substituted.

54. The method of claim 53, wherein the alkane is substituted with O.

55. The method of claim 52 wherein the alkane consists of from about 5 to about 15 carbons.

56. The method of any of claims 46 to 48, wherein the reactive portion comprises a polyethylene glycol.

57. The method of any of claims 23 to 25 and 47, wherein the terminal portion comprises a methacrylate moiety.

58. The method of any of claims 23 to 25 and 47, wherein the terminal portion is derived from 12-methacryloyloxydodecylpyridinium bromide.

59. The method of claim 23, wherein the surface rendered antimicrobial comprises a ligand selected from a group consisting of:

(I)

(II)

-continued (III)

(IV)

and (V)

wherein, x, y and n are independently integers from 0 to 100.

60. The method of claim 23, wherein the polymer substrate is a medical device.

61. The method of claim 60, wherein the medical device is implantable.

62. The method of claim 23, wherein the polymer substrate is a breast implant.

63. The method of claim 24, wherein the polymer substrate comprises polydimethylsiloxane.

64. The method of claim 23, wherein the anti-microbial compound is selected from a quaternary ammonium compound or a phosphonium compound.

65. The composition of claim 1, wherein area density of the anti-microbial compound on the surface of the polymer substrate is about $1\times10^{14}$ molecules/cm$^2$ to about $1\times10^{19}$ molecules/cm$^2$.

66. The composition of claim 65 wherein the area density of the anti-microbial compound on the surface of the polymer substrate is from about $1\times10^{15}$ molecules/cm$^2$ to about $1\times10^{18}$ molecules/cm$^2$.

67. The method of claim 23, wherein area density of the anti-microbial compound on the surface of the polymer substrate is about $1\times10^{14}$ molecules/cm$^2$ to about $1\times10^{19}$ molecules/cm$^2$.

68. The method of claim 67, wherein the area density of the anti-microbial compound on the surface of the polymer substrate is from about $1\times10^{15}$ molecules/cm$^2$ to about $1\times10^{18}$ molecules/cm$^2$.

* * * * *